United States Patent [19]

Cable

[11] Patent Number: 4,628,741
[45] Date of Patent: Dec. 16, 1986

[54] TENSILE TESTING MACHINE

[75] Inventor: Michael J. Cable, Maldon, England

[73] Assignee: Dynapert-Precima Limited, Colchester, England

[21] Appl. No.: 765,518

[22] Filed: Aug. 14, 1985

[51] Int. Cl.$^4$ ............................................. G01N 3/08
[52] U.S. Cl. ..................................................... 73/826
[58] Field of Search ................. 73/788, 791, 795, 800, 73/806, 817, 826, 827, 828, 830, 831, 833, 834, 789

[56] References Cited

U.S. PATENT DOCUMENTS

| | | | |
|---|---|---|---|
| 2,217,080 | 10/1940 | Ruch | 73/806 |
| 2,473,517 | 6/1949 | Freedman | 73/817 |
| 2,555,633 | 6/1951 | Lomins | 73/800 |
| 2,621,512 | 12/1952 | Guimbretiere et al. | 73/830 |
| 2,751,784 | 6/1956 | Gershberg | 73/806 |
| 2,911,823 | 11/1959 | Nistico et al. | 73/795 |
| 3,220,250 | 11/1965 | Strandquist et al. | 73/800 |
| 3,289,469 | 12/1966 | Wentzell et al. | 73/817 |
| 3,533,284 | 10/1970 | Slemmons et al. | 73/817 |
| 4,073,185 | 2/1978 | Grittin | 73/833 |
| 4,081,994 | 4/1978 | Yamawaki et al. | 73/806 |

FOREIGN PATENT DOCUMENTS

| | | | |
|---|---|---|---|
| 559748 | 7/1958 | Canada | 73/834 |
| 140601 | 3/1960 | U.S.S.R. | 73/817 |
| 230488 | 1/1967 | U.S.S.R. | 73/800 |

Primary Examiner—Michael J. Tokar
Assistant Examiner—Robert R. Raevis
Attorney, Agent, or Firm—William F. White

[57] ABSTRACT

Testing machines for appyling a loading to a test specimen are required in the electronics industry for tensile testing fine wire and tape peel force. Suitable machines are known but have been cumbersome, slow to re-set and also rather expensive. By the invention load testing machines are provided e.g. for tensile testing of fine wires or tape peel force testing comprising first and second clamp means (6, 10), one fixed the other moveable linearly, between which a specimen is clamped, and a motor (32) arranged to move the moveable clamp means (10), conveniently through a rack (46) and pinion (44) system and a clutch (42). The machine further comprises means (18) to return the moveable clamp means (10) to an initial position in which the clamp means (6, 10) are spaced apart by a predetermined initial spacing when the clutch (42) is disengaged. This provides rapid re-setting of the machine for a further test.

12 Claims, 5 Drawing Figures

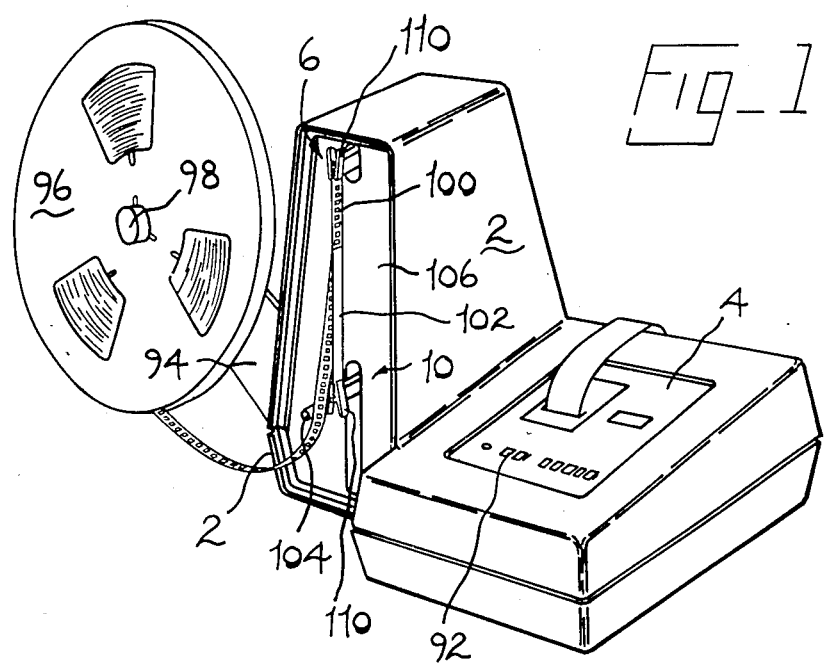
Fig_1
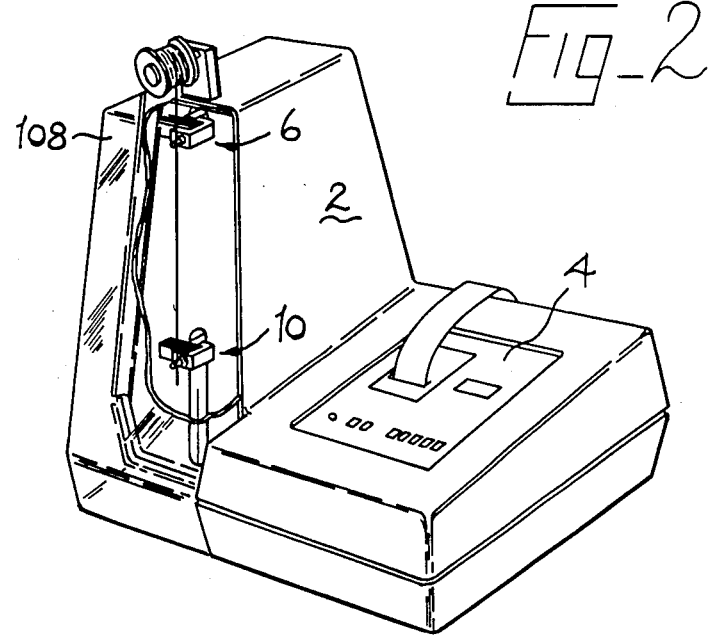
Fig_2

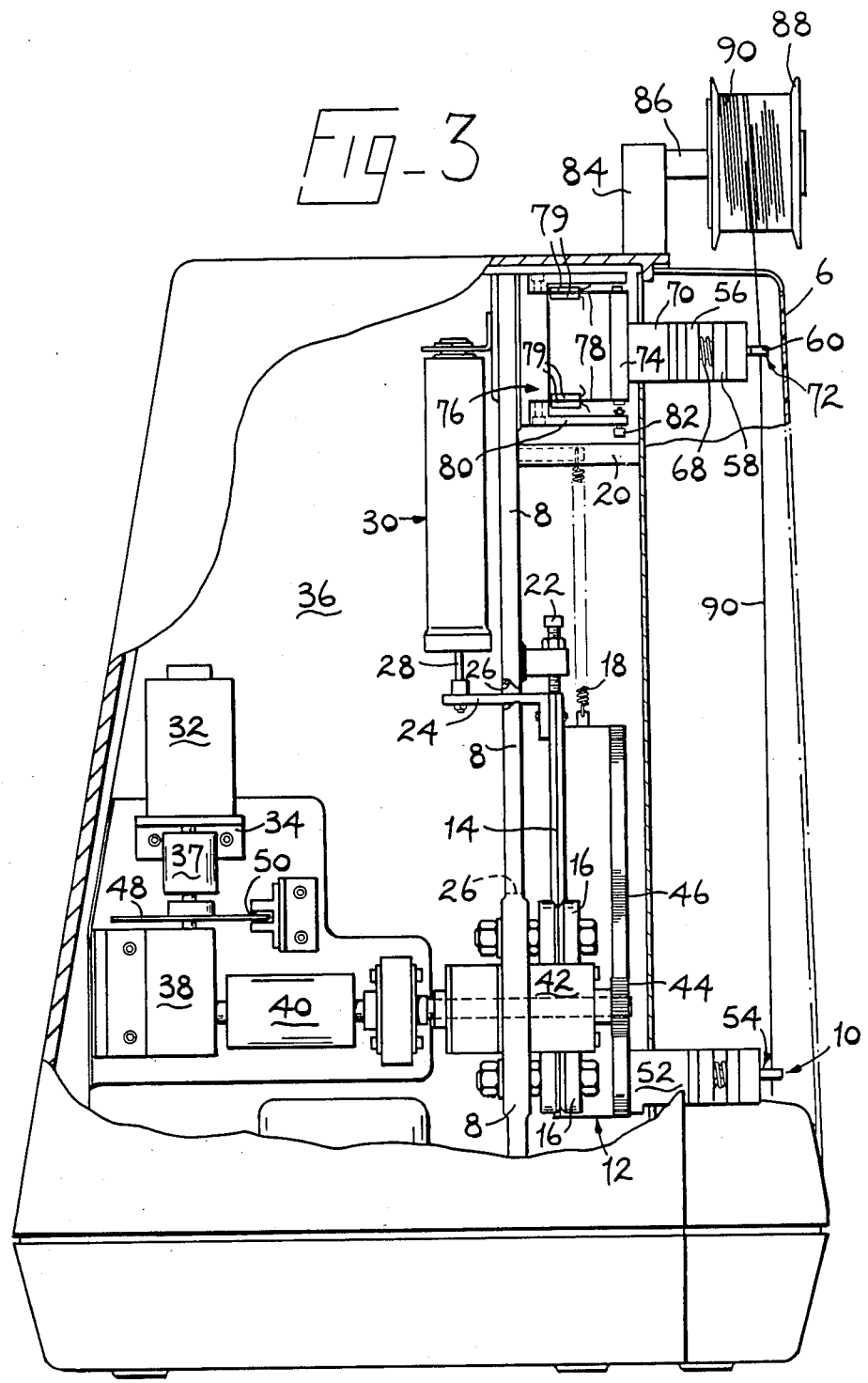

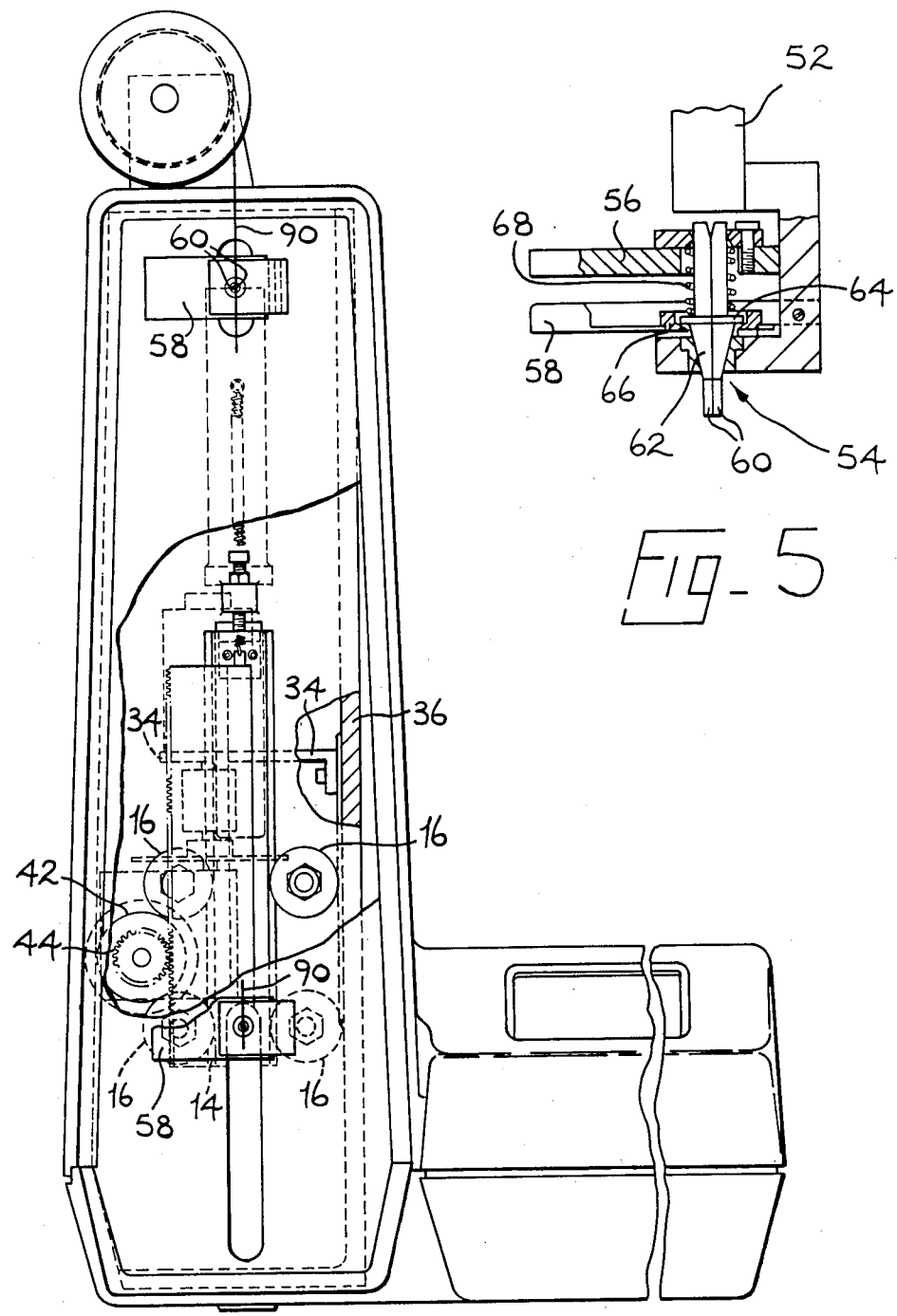
Fig_5
Fig_4

TENSILE TESTING MACHINE

FIELD OF THE INVENTION

This invention is concerned with a testing machine for applying a loading to a test specimen, for example fine wire or pressure sensitive adhesive tape.

BACKGROUND OF THE INVENTION

Fine wires are used in the semi-conductor and electronics industries, for example for wire bonding and it is important to ensure that the wire used has adequate tensile strength, otherwise there is a substantial risk that wires will break during manufacture of components or in their use, leading to circuit failures. Also in the electronics industry, electronic components are often packaged in pockets in plastics or cardboard tapes, being retained in the pockets by a cover tape bonded to the pocketed tape by a suitable adhesive, for example a hot melt adhesive, which is such as to allow the cover tape to be peeled off so that the components can be removed from the pockets. In order to ensure that machines using the tape-packaged components function satisfactorily, it is necessary to check the peel force needed to remove the tape, to ensure that the tape will be cleanly peeled off during use.

Currently available testing machines are unsatisfactory for both of these purposes in that most testing machines which are generally suitable for use for the above described purposes are designed to cope with a very wide range of loadings which makes them unacceptably expensive for the purpose of merely testing fine wire or the peel force required to peel the cover tape off tape-packaged electronic components (the loadings in both instances being of the same order). Furthermore, many known machines are, in general, too slow and inconvenient in operation to be useful for the purposes discussed above.

SUMMARY OF THE INVENTION

A testing machine according to the invention comprises holding means by which a specimen to be tested can be mounted; suitably the holding means comprises first holding means including first clamp means secured on a frame of the machine and second holding means including second clamp means secured on a carriage moveable on the frame so that the second holding means is linearly moveable relative to the first holding means. A testing machine according to the invention further comprises drive means for relatively moving the holding means from an initial relation whereby to apply a loading to the specimen mounted by the holding means. The drive means suitably comprises a motor, preferably a constant speed motor, and a gear arrangement mounted on the frame of the machine. The drive means may be arranged to drive a pinion in the operation of the machine, the pinion engaging a rack and the construction and arrangement being such that relative movement of the holding means is effected by the rack and pinion. A machine according to the invention may comprise means, preferably a clutch, by which the drive means can be disconnected from the holding means when a test has finished and means, preferably comprising a spring, which returns the disconnected holding means to the initial relation. Where a machine according to the invention comprises a clamp means mounted on a carriage as hereinbefore mentioned, means which returns the disconnected holding means is preferably arranged to return the carriage to an initial position in which the first and second clamp means are spaced apart by a predetermined initial spacing. Drive means of a machine according to the invention comprising a constant speed motor is so constructed and arranged as to move the holding means relative to one another to apply the loading to a test specimen at a constant rate.

A machine according to the invention preferably comprises means for measuring the loading applied to the specimen and means for measuring the relative movement between the holding means. Conveniently, a machine in accordance with the invention may comprise means, conveniently comprising a photoelectric system, for counting the revolutions of the drive means to measure the relative movement between the holding means.

A machine according to the invention may comprise means initiating disconnection of the drive means from the holding means when a test has finished, for example means detecting breakage of the test specimen, a timer which operates a predetermined time interval after commencing a test, or means detecting relative movement of the holding means through a predetermined distance.

BRIEF DESCRIPTION OF THE DRAWINGS

The above and other features of the invention will now be particularly described with reference to the accompanying drawings in which:

FIG. 1 is a perspective view of a tape peel force testing machine;

FIG. 2 is a perspective view of a tensile testing machine for wire;

FIG. 3 is a view partly in section and with parts broken away of the tensile testing machine shown in FIG. 2;

FIG. 4 is a front view, partly in section and with parts broken away of the tensile testing machine; and FIG. 5 is a view showing jaws of clamp means of the tensile testing machine.

DESCRIPTION OF THE PREFERRED EMBODIMENT

There now follow detailed descriptions, to be read with reference to the accompanying drawings of two machines for applying a loading to a test specimen, namely a tensile testing machine and a tape peel force testing machine. It will be realised that these machines have been selected for description to illustrate the invention by way of example and not of limitation of the invention.

The wire tensile testing machine and the tape peel force testing machine are generally similar in construction, except as hereinafter described, and for convenience only the tensile testing machine will therefore be described in detail.

The illustrative tensile testing machine comprises a frame 2 by which is mounted the mechanical testing apparatus and a control system comprising electronic computer means by which the testing machine is controlled and which calculates results; an output printer 4 is also mounted in the frame. The illustrative tensile testing machine comprises holding means including first clamp means 6 secured on an upright member 8 of the frame 2 and second clamp means 10 secured on a carriage 12.

The carriage 12 comprises rail means 14 received between four guide wheels 16 mounted for rotation on the upright member 8; the carriage 12 is thus guided for vertical movement and the wheels 16 are adjusted so that there is little or no play, the carriage 12 thereby being accurately mounted for vertical sliding movement. The carriage 12 is urged to an uppermost initial position by a spring 18 extending between the carriage and a cross member 20 of the frame 2. This initial position is determined by engagement of an adjustable stop screw 22 with the carriage 12. The stop screw 22 is adjusted in the course of manufacture of the testing machine so that the first and second clamp means are spaced apart by a predetermined initial spacing. This spacing may be checked during the course of operation of the illustrative testing machine and adjusted by means of the stop screw 22 should this prove necessary.

A bracket 24 projects horizontally from the carriage 12 through a slot 26 in the upright member 8. A piston rod 28 of a pneumatic, damping piston and cylinder arrangement 30 mounted on the upright member 8, is secured to the bracket 24. The damping piston and cylinder arrangement 30 is intended to cushion the vertical return movement of the carriage 12 to its initial position (in which it is shown in FIG. 3). A constant speed electric motor 32 is mounted on a bracket 34 secured to a rear plate member 36 of the frame 2 lying in a vertical plane perpendicular to the vertical plane in which the upright member 8 is disposed. An output shaft of the motor 32 is connected, through a coupling 37, to a reduction gearing system 38. The reduction gearing system 38 drives a pinion 44, through an overload clutch coupling 40 and an electromagnetic clutch 42.

The pinion 44 is mounted in driving engagement with a rack 46 fixed to the carriage 12. A notched disc 48 is secured to a shaft of the gearing system 38, the disc having evenly spaced notches around a peripheral region. The peripheral region of the disc passes through a groove 50 of a photoelectric system; the peripheral region of the disc 48 is arranged, as it passes through the groove 50, to intercept a beam of light directed at a photosensitive device so that rotation of the disc creates a series of electrical pulses each indicating rotation of the disc by the spacing between the notches. In this way the rotation of the gearing system 38 is measured and indicated digitally. As the gearing system 38 is a reduction gearing with a known reduction ratio, and assuming that both the coupling 40 and clutch 42 are engaged, rotation of the disc 48 thus provides a digital representation of the amount of rotation of the pinion 44. The pinion 44 is engaged with the rack 46 so that there is little or no play between the teeth of the pinion and rack and the teeth of both rack and pinion are precisely machined: the pulses generated by rotation of the disc 48 are therefore indicative of the distance moved by the rack 46 and thus of the distance moved by the carriage 12 to which the rack 46 is fixed and of the second clamp means 10 fixed to the carriage. The photoelectric system is arranged to record a distance increment every eight pulses which is equivalent to half a thousandth of an inch (about 0.0127 mm). The overall accuracy of the distance measurement is about ±0.1% equivalent to ±10 thousandth's of an inch, that is about 0.254 mm.

The second clamp means comprises a bracket 52 fixed to the carriage 12, the bracket 52 mounting at its front end a spring collet 54. The spring collet 54 comprises a foundation plate 56 fixed to the bracket 52 and an operating plate 58 pivotally mounted on the bracket 52. A pair of collet jaws 60 are mounted with a conical portion 62 of the jaws received in a corresponding conical seating in the bracket 52. A collar 64 at a base of the conical portion 62 bears against a shoulder portion 66 in the operating plate 58. A compression spring 68 acts between the collar 64 and the foundation plate 56 to urge the conical portion 62 into the corresponding conical seating in the bracket 52, the two jaws 60 thereby being urged towards one another. When the plate 58 is pivoted by an operator towards the foundation plate 56, the jaws 60 are moved against the action of the spring 68 to lift the conical portion 62 from the seating in the bracket 52. The construction and arrangement is such that as the jaws 60 are so moved, they part at a center line allowing introduction of a specimen to be tested. Upon release of the operating plate 58, the spring 68 again urges the jaws so that the conical portion 62 is engaged firmly in its conical seating, thereby urging the gripping faces of the jaws towards one another and thus gripping the specimen between the jaws 60.

The first clamp means 6 also comprises a bracket 70 at a front end portion of which is carried a spring collet 72 similar to the collet 54, the collet 72 being vertically aligned above the collet 54. The bracket 70 is mounted on a vertical member 74 of a strain gauge system 76. The vertical member 74 extends between two horizontal spring members 78 to which it is secured at front end portions thereof. Four strain gauges 79 are mounted at rear ends of each of the spring members 78 and connected to form a bridge network. Application of a load to the bracket 70 transmits the load through the vertical member 74 and spring members 78 to the strain gauges 79 which are calibrated to give a signal indicative of the load applied. The load resolution is such that an accuracy of about ±0.1 grams is achieved.

The strain gauge system 76 is fixed to the upright member 8. A bracket 80 of the strain gauge system 76 projects beneath the lower most one of the spring member 78 and carries at its front end portion a stop screw 82. The stop screw 82 is positioned in alignment with the vertical member 74 and is so adjusted as normally to be spaced slightly from the vertical member 74 so that should an excessive load by applied to the bracket 70, the spring member 78 will yield until the vertical member 74 engages the stop screw 82, whereupon the vertical member 74 and bracket 70 will be supported through the bracket 80 directly by the upright member 8, thereby avoiding excessive strain on the spring members 78.

Mounted on an upper portion of the frame 2 is means for supporting a specimen to be tested. This means, in the illustrative tensile testing machine, comprises a support bracket 84 which carries an axle 86 on which is rotatably mounted a spool 88 on which wire 90 to be tested is wound. The spool 88 is positioned in alignment with the clamp means 6, 10 so that wire 90 to be tested can readily be unwound from the spool, fed between the jaws 60 of the collets 72, 54 and clamped therebetween.

A front portion of the machine is enclosed by a hinged transparent plastic cover 108 whilst the test is underway which gives protection to the test piece during the test.

In the operation of the illustrative tensile testing machine in testing fine wire, the machine is arranged to deal with wire or fibres which have a breaking load of between 0 and 200 grams, for example the fine wires commonly used in wire bonding in the semi-conductor industry. Such wires are commonly of gold or aluminium and may commonly be as little as 30 microns in diameter. With the holding means, viz. the first and second clamp means 6, 10 in their initial relation, (that is with the second clamp means 10 in its initial, uppermost position) the first and second clamp means are spaced apart by a predetermined initial distance. A specimen of wire 90 to be tested is unwound from a spool 88 mounted on the axle 86 and clamped by the spring collets 72, 60 of the first and second clamp means 6, 10. The first and second clamp means are constructed so that the distance between the jaws of the collets is ten inches (254 mm) so that the specimen clamped thereby has a nominal length of ten inches (254 mm). Care is taken that the specimen to be tested does not have undue slack between the collets 72, 54 and also that the specimen is not taut. If an attempt is made to mount a taut specimen between the clamp means 6, 10 there is a substantial risk that the specimen will be subjected to undue loading during the mounting of the specimen in the clamp means 6, 10 and thus damaged so that the subsequent test will not give a true record of the properties of the specimen being tested: if this is done, the machine detects this and stops, indicating that the specimen is preloaded.

The illustrative tensile testing machine will have already been connected to a suitable power supply and switched on so that the motor 32 will be running at its constant speed (a suitable motor may run at a speed of 1500 revolutions per minute); however, the electromagnetic clutch 42 will at this time remain disengaged. Having mounted a specimen to be tested in the clamp means 6, 10 as hereinbefore described, an operator presses a start switch 92 to commence the test. Operation of the start switch causes the electromagnetic clutch 42 to engage thereby transmitting the drive from the motor 32 to the pinion 44 and starting to move the rack 46 and thus the carriage 12 to which the rack is fixed, downwardly (viewing the FIGS. 2 to 4 of the drawings) so that the distance between the first and second clamp means 6, 10 gradually increases. The speed of the motor 32 and the ratios of the reduction gearing system 38 are such that the strain rate is 10% per minute, that is, the distance between the first and second clamp means increases by one inch (25.4 mm) every minute.

Operation of the start switch 92 at the same time starts a distance recorder of the control system, the recorder being set to have as the initial distance a distance of ten inches (254 mm), that is the spacing between the jaws 60 of the collets 54, 72 when the clamp means 6, 10 are in their initial relation. The strain gauge system 76 is also actuated at this time to measure strain and to record the strains measured. Should the strain gauge system 76 indicate, when the start switch is operated, that the test specimen is already loaded (that is that the specimen may have been stretched during mounting between the clamp means) a signal is given which results in the test being stopped and recorded as a failure. The control system of the machine is arranged to record the distance moved by the second, moving collet 54 and the load registered by the strain gauge system 76 at incremental intervals of distance. The control system is also arranged to record the maximum load indicated by the strain gauge system 76. The control system is designed to include a factor in the recording of the distance moved by the moveable second clamp means 10 to compensate for movement of the bracket 70 of the strain gauge system caused by the load applied thereto.

Assuming that there is no initial failure, the motor 32 continues to drive the carriage downwardly thereby increasing spacing between the first and second clamp means 6, 10. Pulses generated by the notched disc 48 interacting with the photoelectric system are transmitted to the distance recorder and added to the initial distance recorded of ten inches (254 mm). After the carriage 12 has moved a small distance, the strain gauge system 76 should start to record a load on the test specimen. However, if the specimen was mounted between the clamp means 6, 10 in too slack a manner, the distance moved by the carriage 12 before the strain gauge system 76 starts to record any load on the specimen will be too great to allow a satisfactory test. The control system of the tensile testing machine is therefore arranged so that should the distance between the first and second clamp means 6, 10 reach a predetermined distance before the strain gauge system 76 records any load on the specimen, an alarm signal is given and the test is indicated to be a failure due to the slackness of the specimen.

Should the strain gauge system 76 start to record a load on the test specimen before the failure distance between the clamp means 6, 10 is reached the test will continue with the motor 32 moving the carriage 12 and thus the second clamp means 10 at the rate previously mentioned. As the spacing between the first and second clamp means 6, 10 gradually increases the load measured by the strain gauge system 76 and recorded by a suitable recorder of the machine control system gradually increases. After some time, the rate of increase will reduce as the test specimen starts to yield and the load recorded may ultimately fall.

Finally, in most instances, the test specimen will break. Breakage of the test specimen will of course mean that the load registered by the strain gauge system 76 will drop substantially immediately to zero. The control system of the tensile testing machine, on recognising breakage of the specimen by the sudden falling of the load to zero immediately signals the electromagnetic clutch 42 to disengage, thus allowing the carriage 12 to be returned by the spring 18 to its initial position, the pinion freely rotating as the carriage returns. The return movement of the carriage is cushioned by the damping piston and cylinder arrangement 30 which acts as a dash pot ensuring that the carriage 12 is not returned violently to its initial position.

On recognizing breakage of the test specimen not only does the control system signal disengagement of the clutch 42, but also causes print out of the test results on the output printer 4. The control system may be arranged to calculate and print various results but will normally be arranged to print out the maximum tensile strength (that is the maximum load recorded), the ultimate tensile strength (that is the load at which the test specimen breaks) and the percentage elongation at break. Elongation at break is calculated using as the base length of the test specimen the initial spacing of the clamps (ten inches) plus the distance moved by the second clamp means 10 when the strain gauge system 76 first records a load (that is when any slack in the test specimen has been taken up): from that point the further distance moved until breakage is, of course, the extension of the test specimen. The printer is also usually programmed to print a graph of load versus extension.

The control system may also be arranged to calculate the proof stress.

Occasionally the specimen may slip in one of the collets 54, 72: if this happens, there will usually be a sudden fall in the load recorded by the strain gauge system 76, followed by a further increase. The control system of the tensile testing machine is arranged to recognize slippage and signal a failure of the test, signalling disengagement of the clutch 42 and terminating the test.

The use of the electromagnetic clutch 42 allows substantially instantaneous re-setting of the testing machine for testing a new specimen, thus increasing the test rate, especially in comparison with previously used screw operated tensile testing machines. In a screw system it is necessary to screw the moveable clamp means back to its initial position (that is the reverse movement to the movement occurring in the actual test): because of the fine pitch of the screw necessary to give the fine movement which occurs in the actual test it is not possible readily to reverse roles of driving and driven member to return the moveable jaw very rapidly to its initial position using a screw. The rack and pinion drive system is especially suitable for rapid re-setting in so far as the role of driving and driven member can readily be reversed. Other transmission systems which may be suitable include chain (or toothed belt) and sprocket systems, although these may give problems should the belt or chain prove to be somewhat extensible for example such machines may need more frequent adjustment: the rack and pinion drive system is preferred. It will be appreciated that the spring 18 ensures that the rack and pinion are maintained in positive meshing engagement so that the driving face of the teeth of the pinion 44 are always in engagement with the same face of the teeth of the rack when the machine is carrying out a test so that no errors are likely to arise due to any play between the rack teeth and pinion teeth.

The overload clutch coupling 40 is arranged to allow slippage of the drive between the gearing system 38 and the electromagnetic clutch 42 should a safe loading of the testing machine be exceeded during a test—this also will result in the test being aborted.

The control system of the illustrative tensile testing machine also comprises means which will terminate the test when the holding means have moved relatively through a predetermined distance (viz. three inches, 76·2 mm) from the start of the test, not as a "fail" but as a successful test causing the control system to initiate the same operations that are initiated by breakage of the test specimen. The tensile testing machine also comprises an overrun micro switch mounted in alignment with the carriage 12 so that should the other termination systems fail, the carriage will operate the micro switch, disengaging the clutch and terminating any test underway.

It will be appreciated that in the illustrative tensile testing machine the collet jaws are so constructed and arranged that the specimen to be tested will not be damaged by the jaws when gripped—should the jaws grip the specimen, especially a fragile and thin wire, too tightly the specimen may be damaged which could lead to premature breakage and generally inaccurate test results.

Whereas the strain gauge system in the illustrative tensile testing machine is associated with the fixed clamp means, the strain gauge system could be associated with a moveable clamp means in a machine otherwise similar to the illustrative tensile testing machine, although in this instance the connections involved would be more complicated.

As hereinbefore mentioned the tape peel force testing machine is substantially identical in construction to the tensile testing machine described hereinbefore apart from a few minor details. One difference in detail which arises is that a different gearing system 38 is used so that the rate of movement of the second clamp means 10 of the tape peel force testing machine is five inches (about 127 mm) per minute as compared with the one inch per minute movement rate in the tensile testing machine. The tape peel force testing machine (see FIG. 1) comprises, instead of the support bracket 84 at the top of the machine, a support bracket 94 secured to a side portion of the machine frame 2 and comprising an axle on which a reel 96 is mounted for rotation and retained in place by a nut 98 which can readily be removed to change reels. The reel carries a pocketed component tape 100, having a cover tape 102 adhered by a suitable adhesive (which will allow the cover tape to be peeled off when the components are to be used) to the pocketed tape to retain electronic components in the pocketed tape. The illustrative tape peel force testing machine also comprises a tape guide 104 mounted on a front plate 106 of the machine frame.

The first and second clamp means 6, 10 of the tape peel force testing machine differ from those of the tensile testing machine in that instead of the spring collets 54, 72, the first and second clamp means 6, 10 are provided with spring clips 110 of the type known as crocodile clips, positioned with the jaws thereof facing one another. However, any convenient form of clip may be used provided that its holding force is sufficient to grip the appropriate tape without the tape slipping during the test, while yet not damaging the tape to such an extent that the tape breaks or itself yields giving a false load reading.

In the operation of the illustrative tape peel force testing machine a reel of tape to be tested is mounted on the support axle carried by the bracket 94 and locked in place by the nut 98. The tape is passed round the tape guide 104 and a leading end portion of the cover tape 102 is separated manually from a leading end portion of the pocketed tape 100. The pocketed tape 100 is then clamped by the spring clips 110 to the first clamp means 6 and the leading end portion of the cover tape 102 is clamped by the appropriate spring clip to the second clamp means 10. The peel point of the tape is thus between the first clamp means 6 and the second clamp means 10 and is preferably arranged to be sufficiently close to the first clamp means 6 that the second clamp means when it is moved by the motor 32 pulls the leading end portion of the cover tape 102 in a plane in which the clamp means 6, 10 lie, substantially coplanar with the leading end portion of the pocketed tape 100 (see FIG. 1).

In carrying out a tape peel force test the control system of the testing machine is preferably arranged to record the maximum peel force required during the test and the minimum peel force required and to plot a graph of load employed against distance moved by the second clamp means.

As no breakage should occur during normal operation of the peel force testing machine, the test will usually be terminated by the control system after the second, moving clamp means 10 has been moved through a predetermined distance of three inches (76·2 mm).

However, should breakage or slippage occur the control system is arranged to recognize this and indicate a test failure while terminating the test by disengaging the clutch 42 as hereinbefore described with reference to the tensile testing machine.

Should the (control system) fail to terminate the test as mentioned above, the test will ultimately be terminated by engagement of the carriage 12 with the micro switch mentioned previously.

Both of the illustrative machines described herein are of simple construction and are easy to use. The machines are rapidly re-set for further tests. Because the machines are designed to deal with a relatively small load range and to handle a restricted class of products, the illustrative machines are also relatively inexpensive.

I claim:

1. A testing machine for applying a load to a test specimen, said machine comprising:
    a frame;
    first means for clamping the test specimen, said first clamping means being secured to said frame;
    second means for clamping the test specimen, said second clamping means being secured on a carriage moveable on said frame;
    a motor, mounted on said frame and arranged to drive a pinion through a clutch;
    a rack secured to the carriage and in engagement with said pinion so as to move said carriage associated with said second clamping means and thereby move said second clamping means away from said first clamping means; and
    means, operative when said clutch is disengaged, for returning said carriage to an initial position in which said first and second clamping means are spaced apart by an initial predetermined spacing.

2. The testing machine according to claim 1 comprising means for initiating disengagement of the clutch when a test has finished.

3. The testing machine according to claim 2 wherein said means for initiating disengagement of the clutch comprises means for detecting breakage of the test specimen.

4. The testing machine according to claim 2 wherein said means for initiating disengagement of the clutch comprises means for detecting relative movement of said first and second holding means through a predetermined distance.

5. The testing machine according to claim 2 wherein said means for initiating disengagement of the clutch comprises a timer which operates to initiate disengagement at a predetermined time interval after commencing a test.

6. The testing machine according to claim 1 wherein said means for returning the holding means to the initial relation comprises a spring.

7. The testing machine according to claim 6 further comprising cushioning means arranged to cushion the return of the holding means.

8. The testing machine according to claim 1 wherein said motor is a constant speed motor.

9. The testing machine according to claim 1 further comprising means for counting revolutions of said motor so as to measure the movement of the second clamping means.

10. The testing machine according to claim 9 wherein the counting means comprises a photoelectric system.

11. The testing machine according to claim 1 further comprising means for measuring the load applied to the specimen.

12. The testing machine according to claim 11 wherein said means for measuring the applied load comprises a strain gauge system located between said first and second clamping means.

* * * * *